(12) United States Patent  
Mueller et al.

(10) Patent No.: US 8,086,083 B2  
(45) Date of Patent: Dec. 27, 2011

(54) LIGHT GUIDING FLUID CONDUIT HAVING A LIQUID-FILLED INTERSPACE BETWEEN INNER AND OUTER CONDUITS

(75) Inventors: Beno Mueller, Waldbronn (DE); Bertram Beigel, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 378 days.

(21) Appl. No.: 12/403,005

(22) Filed: Mar. 12, 2009

(65) Prior Publication Data

US 2009/0230028 A1    Sep. 17, 2009

(30) Foreign Application Priority Data

Mar. 13, 2008    (EP) .................................... 08102573

(51) Int. Cl.  
*G02B 6/02* (2006.01)  
*G02B 6/00* (2006.01)

(52) U.S. Cl. .......................... 385/125; 385/147

(58) Field of Classification Search .................... 385/12, 385/125, 126, 129, 147; 422/58, 82.05; 356/246, 356/338, 339, 336, 340, 343  
See application file for complete search history.

(56) References Cited

U.S. PATENT DOCUMENTS

| | | | | |
|---|---|---|---|---|
| 3,641,332 A * | 2/1972 | Reick et al. | .................... | 362/582 |
| 5,570,447 A | 10/1996 | Liu | | |
| 5,604,587 A * | 2/1997 | Che et al. | ....................... | 356/246 |
| 6,542,231 B1 * | 4/2003 | Garrett | ............................ | 356/246 |
| 2002/0102183 A1 * | 8/2002 | Uchimura | ......................... | 422/58 |
| 2006/0207673 A1 * | 9/2006 | O'Brien et al. | ................. | 138/114 |

FOREIGN PATENT DOCUMENTS

EP    1229322 A1    8/2002  
EP    1577012         9/2005

OTHER PUBLICATIONS http://www.chem.agilent.com/en-us/products/instruments/lc/1200serieshighthroughputlcuvms/pages/default.aspx.  
http://en.wikipedia.org/wiki/Column_chromatography.

* cited by examiner

*Primary Examiner* — Akm Ullah

(57) ABSTRACT

A fluid conduit comprises an inner conduit configured for conducting a fluid, and an outer conduit circumferentially enclosing the inner conduit. The outer conduit's inner diameter is larger than the inner conduit's outer diameter, with an interspace being formed between the inner conduit's outer surface and the outer conduit's inner surface. The interspace between the inner conduit's outer surface and the outer conduit's inner surface contains an interspace liquid. The inner conduit is configured for guiding light coupled into the inner conduit, and dependent on the light's angle of incidence, total reflection occurs at a boundary between the inner conduit's outer surface and the interspace between the inner conduit and the outer conduit.

19 Claims, 6 Drawing Sheets

LIGHT GUIDING FLUID CONDUIT HAVING A LIQUID-FILLED INTERSPACE BETWEEN INNER AND OUTER CONDUITS

This application claims priority from European Patent Application, No. EP08102573.6 filed on 13 Mar. 2008, which is incorporated by reference in its entirety.

BACKGROUND ART

The present invention relates to a fluid conduit, a detection system comprising a fluid conduit, and a fluid separation system comprising the detection system.

For detecting optical properties of a fluid, a beam of light may be passed through a volume of the fluid, and after it has passed through a certain volume of the fluid, it is determined how the light has been altered during its passage through the volume of fluid. For example, the fluid may comprise light-absorbing moieties that absorb light, and as a consequence, the intensity of the light may be attenuated at certain wavelengths during its passage through the fluid. Alternatively or additionally, the fluid may affect the polarization of light passing through the fluid.

Fluid conduits for use in detection cells are adapted both for conducting a fluid and for guiding light. To provide for detection with high sensitivity, the light has to travel a certain path in the fluid before it is detected.

Fluid conduits known in the art often use an unprotected outer capillary wall, which can be contaminated by dust or chemicals in the surrounding air. In other solutions, the outer surface of the fluid conduit might be protected by special coatings such as BeF2, BeF2-RbF and others (as disclosed e.g. in U.S. Pat. No. 5,570,447) or by Teflon AF polymer. In EP 1229322 A1, a flexible protection tube is formed outside an inner tube to hold shape of the inner tube.

In high performance liquid chromatography (HPLC), a liquid has to be provided usually at a very controlled flow rate (e. g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid which may then be identified.

The mobile phase, for example, a solvent, is pumped under high pressure typically through a column of packing medium, and the sample (e.g. a chemical or biological mixture) to be analyzed is injected into the column. As the sample passes through the column with the liquid, the different compounds, each one having a different affinity for the packing medium, move through the column at different speeds. Those compounds having greater affinity for the packing medium move more slowly through the column than those having less affinity, and this speed differential results in the compounds being separated from one another as they pass through the column.

The mobile phase with the separated compounds exits the column and passes through a detector, which identifies the molecules, for example by spectrophotometric absorbance measurements. A two-dimensional plot of the detector measurements against elution time or volume, known as a chromatogram, may be made, and from the chromatogram the compounds may be identified. For each compound, the chromatogram displays a separate curve or "peak". Effective separation of the compounds by the column is advantageous because it provides for measurements yielding well defined peaks having sharp maxima inflection points and narrow base widths, allowing excellent resolution and reliable identification of the mixture constituents. Broad peaks, caused by poor column performance, are undesirable as they may allow minor components of the mixture to be masked by major components and go unidentified.

SUMMARY

It is an object of the invention to provide an improved fluid conduit adapted for conducting a fluid and for guiding light. The object is solved by the independent claim(s). Further embodiments are shown by the dependent claim(s).

A fluid conduit according to embodiments of the present invention comprises an inner conduit adapted for conducting a fluid, and an outer conduit circumferentially enclosing the inner conduit. The outer conduit's inner diameter is larger than the inner conduit's outer diameter, with an interspace being formed between the inner conduit's outer surface and the outer conduit's inner surface. The interspace between the inner conduit's outer surface and the outer conduit's inner surface contains a liquid. The inner conduit is adapted for guiding light coupled into the inner conduit, wherein, dependent on the light's angle of incidence, total reflection occurs at a boundary between the inner conduit's outer surface and the interspace between the inner conduit and the outer conduit.

Within the inner conduit, a flow of fluid is conducted. Furthermore, light is coupled into the inner conduit and traverses the fluid. Due to the presence of the liquid in the interspace having a refractive index lower than the conducted, total reflection of light occurs at the inner conduit's outer surface, as there is a step of refractive index between the inner conduit and the interspace.

Light coupled into the inner conduit is guided along the inner conduit and may interact with the fluid passing through the inner conduit. Therefore, a fluid conduit according to embodiments of the present invention is well-suited for determining optical properties of a fluid passing through the inner conduit.

The outer conduit encloses the inner conduit. The outer conduit protects the inner conduit from dirt, dust and moisture. Therefore, the outer surface of the inner conduit remains dry and clean. This is important, because total reflection mostly occurs at the inner conduit's outer surface. By protecting and sealing the outer surface of the inner conduit, well-defined reflective properties of the inner conduit are accomplished, and the reliability of the inner conduit's optical behavior is improved.

The outer conduit serves as a protection shield. When the outer conduit's surface gets in contact with dirt, dust and moisture, or when the outer conduit is clamped in some kind of mount, this will not have any impact on the optical properties of the fluid conduit.

The inner conduit is preferably made of glass or silica. The outer conduit may also be made of glass or silica or any other suitable material such as metal, ceramics or plastics. The inner conduit as well as the outer conduit might be a capillary preferably with round shape. Any other suitable shape, such as rectangular, might be used as well.

In an embodiment, the interspace is filled with a liquid of the Fluorinert family of 3M, i.e. FC40, which has a refractive index lower than water. Alternatively or in combination Krytox from DuPont might be used as interspace liquid. The Fluorinert liquids are relatively inert and will therefore hardly lead to any modification of the outer surface of the inner conduit.

Embodiments of the invention thus allow that the outer surface of the inner conduit (in other words, the basic liquid core waveguide) is protected against contamination of dust or particles which otherwise may generate straylight and hence deteriorate the light guiding capability of the fluid conduit. Further, the outer surface of the inner conduit is also protected against gaseous contamination, for example by air, oxygen or other chemicals in the ambient air, which could lead to coatings or chemical reactions at the surface and hence changing the optical properties of the surface (e.g. silica surface).

In one embodiment, the length of the outer conduit differs from the inner conduit. The interspace is sealed by adhering the conduits together or by sealing the outer conduit to a connecting member. This can be advantageous as the sealing material is not in contact to the conducted fluid.

In one embodiment, the fluid conduit comprises a liquid conveyance configured to supply the interspace liquid into the interspace. The liquid conveyance may be configured to pressurize the interspace liquid and/or to vary a property of the interspace liquid. Such property can be at least one of: consistency, mixing ratio, electrical capacity, thermal capacity, refractive index, pressure.

The interspace liquid may be used to modify, adapt or vary the thermal behavior of the fluid conduit. Without the interspace liquid, the fluid conduit (provided by the inner and outer conduits and the conducted fluid) typically has a low heat capacity. Also, heat conductivity is typically low without the interspace liquid, due to air surrounding the waveguide. Low heat capacity and conductivity may result to fast and high responsiveness when the temperature of the fluid conduit changes for example in consequence of varying temperatures of the conducted fluid (e.g. a solvent as a mobile phase in an HPLC application). Unstable or varying solvent temperatures are very common e.g. in case of gradient methods in chromatography, since the changing solvent mixtures have different heat capacities. Therefore the heat transfer from or into the cell body varies during the gradient run and may cause changing refractive indices of the liquids. Consequently the optical properties of the system are changed and more or less optical rays will be transmitted by the system. This can lead to apparent absorption effects and may result in analysis errors. There may also be applications, where the opposite behavior can be of advantage, i.e. slow and low responsiveness to temperature variations. The interspace liquid in direct contact to the outer conduit may enhance such behavior, since the extra amount of liquid provided by the interspace liquid posses extra heat capacity and enables heat transfer to outer region of the fluid conduit.

In one embodiment, the liquid in the interspace is provided to be under pressure, e.g. higher than atmospheric pressure. This may lead to a higher pressure resistance of the fluid conduit and may be in particular of advantage in case the inner and/or outer conduit has thin walls, e.g. silica walls, or in miniaturized cells (e.g. based on micromachining techniques). In today's HPLC applications, the applied pressure delivered by the pumps exceed the 1000 bar level. A part of this applied pressure drops off at the fluid conduit (e.g. when applied as a flow cell for detecting separated compounds) according to the flow resistance of the fluid conduit and the liquid path behind the fluid conduit, for example another detector. In case of a blocked capillary, which is not unusual e.g. in mass spectrometer applications, the total pressure delivered by the pump will stress the fluid conduit and may damage the fluid conduit. Also operator misuse can lead to overpressure, e.g. if too high flow rates are applied. In particular fluid conduits made of silica or miniaturized fluid conduits with thin walls are very fragile and suspect to damage. In order to improve characteristics of total internal reflection, the fluid conduit might turn our relatively fragile (e.g. to provide the thickness of the inner capillary wall as small as possible). The smaller the wall thickness the better the light transmission of the cell and the better the effective interaction with the sample. The provision of pressure to the interspace liquid can lead to increased pressure stability of the fluid conduit. For this purpose the liquid can be pressurized, filled into the interspace, and closed e.g. by a sealing and a plug, preferably in a similar way as used for filling dampers in HPLC pumps.

According to a preferred embodiment, for a certain range of angles of incidence, the light is reflected at the boundary between the inner conduit's outer surface and the interspace. If the angle of incidence relative to the surface normal exceeds a critical angle, the light will be totally reflected by the inner conduit.

According to a preferred embodiment, light coupled into the inner conduit is repeatedly reflected at the boundary between the inner conduit's outer surface and the interspace. Preferably, due to total reflection at the boundary between the inner conduit's outer surface and the interspace, the light is guided along the inner conduit. Thus, the light traverses a fluid flowing in the inner conduit.

According to a preferred embodiment of the present invention, the outer conduit is substantially oriented coaxially with the inner conduit. Preferably, the outer conduit is adapted for sealing and protecting the inner conduit. In particular, the inner conduit is protected from dirt, dust and moisture. Dirt, dust and moisture are prevented from adhering to the outer surface of the inner conduit. Because of the interspace formed between the inner conduit and the outer conduit, well-defined reflection at the inner conduit's outer surface are accomplished.

According to a preferred embodiment, the outer conduit's inner surface touches the inner conduit's outer surface at most at a line of contact. The region where the outer conduit touches the inner conduit is very small (relative to the outer surface of the inner conduit) and does not substantially affect the reflective properties of the inner conduit.

According to a preferred embodiment, a spacer is arranged between the inner and the outer conduit. Preferably, spacer is made of one of: carbon, teller, polyamide, polyimide, polyetheretherketone, also referred to as PEEK.

According to a preferred embodiment of the present invention, at one end or at both ends of the fluid conduit, the inner conduit and the outer conduit are welded together. Thus, the interspace between the inner and the outer conduit can be encapsulated and moisture etc. is prevented from entering.

According to a preferred embodiment, a first end of the fluid conduit is adapted for accepting a first optical waveguide, which may be an optical fiber, the first optical waveguide being adapted for coupling light into the fluid conduit. Further preferably, a flow of fluid is supplied to the inner conduit at a first end of the fluid conduit.

According to a preferred embodiment, a second end of the fluid conduit is adapted for accepting a second optical waveguide, which may be an optical fiber, the second optical waveguide being adapted for decoupling light from the fluid conduit. Further preferably, a flow of fluid is withdrawn from the inner conduit at a second end of the fluid conduit.

According to a preferred embodiment of the present invention, the fluid conduit is a detection channel of a detection system. The detection system may e.g. be adapted for analyzing light decoupled from the fluid conduit. The detection system may e.g. be adapted for determining at least one optical property of a fluid passing through the fluid conduit by analyzing light decoupled from the fluid conduit. In particular, the detection system may e.g. be adapted for determining absorbance of a fluid passing through the fluid conduit.

A detection system according to embodiments of the present invention comprises a fluid conduit as described above. The detection system further comprises a first connecting member attached to the fluid conduit's first end. The first connecting member comprises a fluid inlet fluidically coupled to the fluid conduit, the fluid inlet being adapted for supplying a flow of fluid to the fluid conduit. The first connecting member is further adapted for coupling light into the fluid conduit. The detection system further comprises a second connecting member attached to the fluid conduit's second end. The second connecting member comprises a fluid outlet fluidically coupled to the fluid conduit, the fluid outlet being adapted for withdrawing a flow of fluid that has been conveyed through the fluid conduit. The second connecting member is further adapted for decoupling light from the detection channel. The interaction of light with the fluid passing through the inner conduit is used for determining the optical properties of the fluid. The detection system may e.g. be employed for detecting the presence of different sample compounds in the fluid, because the compounds may affect the optical properties of the fluid. Furthermore, concentrations of different sample compounds in the fluid may e.g. be determined by analyzing light that has passed through the fluid conduit. For example, the decrease of intensity of light passing through a fluid sample containing light-absorbing moieties may be related to the concentration of the respective moieties.

According to a preferred embodiment, the detection system comprises first optical waveguide adapted for coupling light into the fluid conduit, whereby the first optical waveguide may e.g. be mounted to the first connecting member.

According to a preferred embodiment, the detection system comprises a second optical waveguide adapted for decoupling light from the fluid conduit, whereby the second optical waveguide may e.g. be mounted to the second connecting member.

According to a preferred embodiment of the present invention, the detection system comprises a light source adapted for supplying light to the fluid conduit. Light emitted by a light source may be coupled to the fluid conduit via an optical waveguide. Alternatively, due to the reliable reflective properties of the fluid conduit, light from the light source may also be coupled directly to the fluid conduit, e.g. by focusing the light onto the inlet of the fluid conduit.

According to a preferred embodiment, the detection system comprises a mercury vapor lamp adapted for supplying light to the fluid conduit. A mercury vapor lamp provides light comprising a continuous range of different wavelengths. Using a mercury vapor lamp, optical properties of the fluid may be examined for a wide range of different wavelengths. Preferably, a lens or a lens system may be employed for coupling a light beam into the fluid conduit. Further preferably, a diaphragm may be used for controlling the aperture of a light beam coupled into the fluid conduit.

According to an alternatively preferred embodiment, the detection system comprises a laser adapted for supplying light to the fluid conduit.

According to a preferred embodiment of the present invention, the detection system is adapted for analyzing light decoupled from the fluid conduit. Preferably, the detection system may determine at least one optical property of a fluid passing through the fluid conduit as a function of time. Further preferably, the at least one optical property is monitored at one or more predefined wavelengths.

According to a preferred embodiment, the detection system is adapted for monitoring absorbance of a fluid passing through the fluid conduit as a function of time. Further preferably, the detection system may e.g. monitor a concentration of light-absorbing species in a fluid passing through the fluid conduit. A certain concentration of a respective light-absorbing species will cause a corresponding reduction of light intensity at one or more characteristic wavelengths where absorption occurs.

According to a preferred embodiment of the present invention, the detection system is a variable wavelength detector, also referred to as a VWD. A variable wavelength detector may monitor light intensity at several discrete wavelengths as a function of time.

According to a preferred embodiment, the detection system is a diode array detector, also referred to as a DAD. A diode array detector comprises an array of photosensitive elements. Using a diode array detector, light intensity of a continuous range of wavelengths may be monitored as a function of time.

Embodiments may comprise at least one of:
an inner diameter of the inner conduit is in the range between 0.01 mm and 0.8 mm, and preferably about 0.3 mm;
an outer diameter of the inner conduit is in the range between 0.1 mm and 1 mm, preferably about 0.4 mm;
an inner diameter of the outer conduit is in the range between 0.1 mm and 1.5 mm, preferably about 0.5 mm;
an outer diameter of the outer conduit is in the range between 0.2 mm and 3 mm, preferably about 0.7 mm;
a width of the interspace is in the range between 0.01 mm and 0.3 mm, preferably about 0.05 mm.

Although the conduit geometric dimensions are denoted here exemplarily by "diameter", it should be noted that the conduit geometry can be of any suitable shape, e.g. circular or non circular cross sections, oval, rectangular, etc. In the latter case the dimensions "diameter" have to be interpreted analogous as edge length or diagonal extent of the conduit shape. Furthermore, the cross section shape of the conduits does not necessarily have to be constant over the entire length of the conduit, but may vary in shape and dimension, e.g. the "diameter" could increase or decrease like a cone or truncated pyramid.

One embodiment comprises a fluid separation system for separating compounds of a sample fluid in a mobile phase. The fluid separation system comprises a mobile phase drive configured to drive the mobile phase through the fluid separation system, a separation unit configured for separating compounds of the sample fluid in the mobile phase, and a detection system, as in the previous embodiments, configured to detect separated compounds of the sample fluid.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable.

The separating device preferably comprises a chromatographic column (see e.g. http://en.wikipedia.org/wiki/Column chromatography) providing the stationary phase. The column might be a glass or steel tube (e.g. with a diameter from 50 μm to 5 mm and a length of 1 cm to 1 m) or a microfluidic column (as disclosed e.g. in EP 1577012 or the Agilent 1200 Series HPLC-Chip/MS System provided by the applicant Agilent Technologies, see e.g. http://www.chem.agilent.com/Scripts/PDS.asp?IPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, under www.agilent.com which shall be in cooperated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 1 shows a fluid conduit according to an embodiment of the present invention. The fluid conduit is adapted for both conducting a flow of fluid and for guiding light that has been coupled to the fluid conduit. The fluid conduit comprises an inner capillary 1 (as an inner conduit 1) that is enclosed by an outer capillary 2 (as an out conduit 2), with an interspace 3 being formed between the inner capillary 1 and the outer capillary 2. The outer capillary 2 is substantially oriented coaxially with the inner capillary 1. The walls of the inner capillary 1 enclose a fluid channel 4, and a flow 5 of fluid may be passed through the fluid channel 4.

The inner capillary 1 and the outer capillary 2 may for example be made of glass or fused silica. The interspace 3 is filled with a liquid, which allows total reflection at a boundary between the inner conduit's outer surface and the interspace 3. Preferably, FC40 or another liquid of the Fluorinert family of 3M is used, which has a refractive index lower than water.

Optionally, a spacer may be placed between the inner capillary 1 and the outer capillary 2, whereby the spacer may for example be made of one of: carbon, teflar, polyamide, polyimide, PEEK. For example, the spacer may be realized as a fabric made of one of these materials. However, it is to be noted that the spacer is an optional element, and that a spacer is not required for proper operation of the fluid conduit.

At the front face 6 of the fluid conduit, the inner capillary 1 and the outer capillary 2 may be welded together, in order to seal the interspace 3. Welding may for example be effected by bringing the front face 6 of the fluid conduit in close vicinity to a laser-spot or a hydrogen flame having a temperature of about 3000° C.

Figure 1:
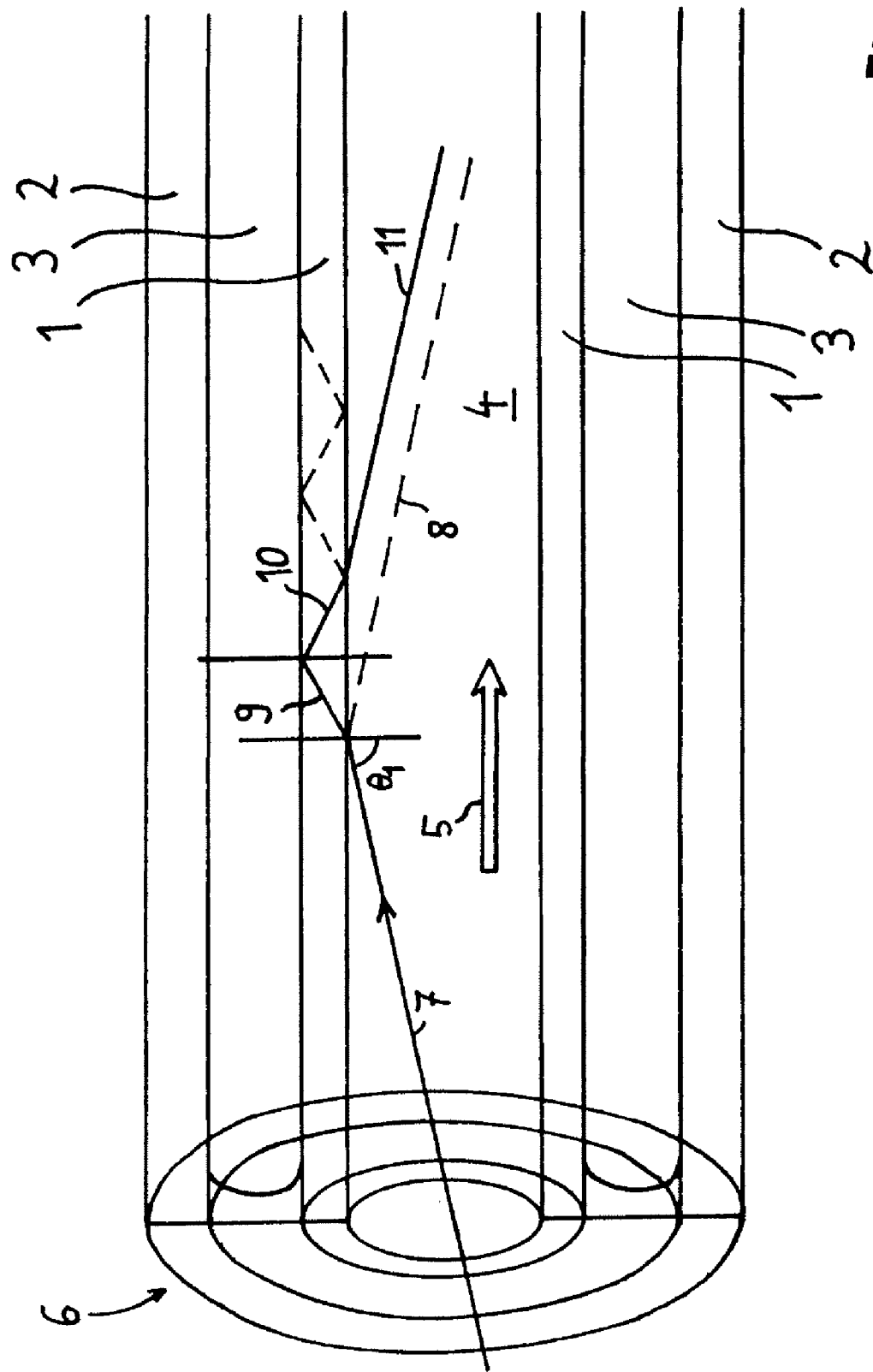
FIG. 1 shows a fluid conduit according to an embodiment of the present invention.

In addition to carrying a flow 5 of fluid, the fluid conduit of FIG. 1 further acts as a light guide adapted for guiding light along the channel 4. An incident light beam 7 that strikes the inner surface of the inner capillary 1 is partially refracted and partially reflected. The reflected beam 8 continuous to propagate in the channel 4. As the refractive index of glass (typically $n_{glass}$=1.5) is greater than the refractive index of the fluid (typically $n_{fluid}$=1.33) in the channel 4, the refracted beam 9 is refracted towards the normal. The refracted beam 9 strikes the outer surface of the inner capillary 1. In case the refracted beam's angle of incidence is greater than a critical angle, total internal reflection occurs at the glass-air-boundary. In this case, the refracted beam 9 is totally reflected at the outer surface of the inner capillary 1, and a reflected beam 10 is redirected towards the channel 4. When reaching the glass-fluid-boundary, most of the intensity of the reflected beam 10 passes the glass-fluid-boundary, and the resulting beam 11 continues propagating within the fluid channel 4. However, a small portion of the intensity of the reflected beam 10 is further reflected at the glass-fluid-boundary and continues propagating within the walls of the inner capillary 1.

DETAILED DESCRIPTION

Figure 2:
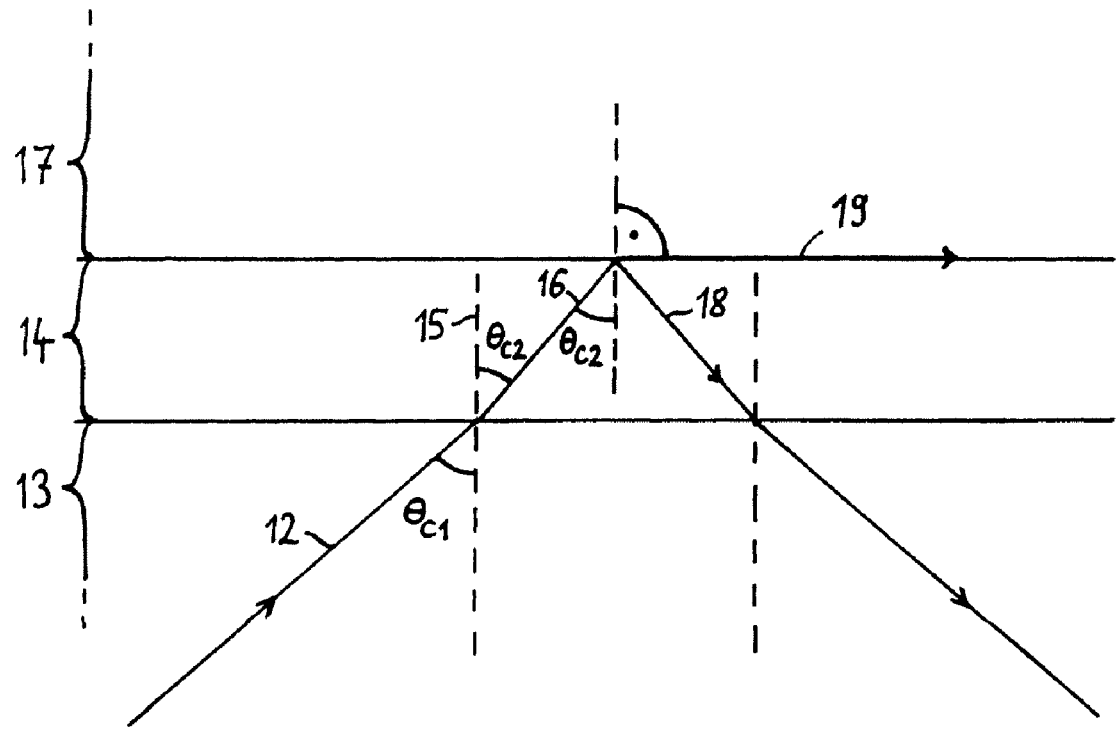
FIG. 2 shows an incident beam of light that is totally reflected at an inner capillary's outer surface.

FIG. 2 illustrates how a critical angle of incidence $\theta_{C1}$ for total internal reflection of a light beam 12 may be determined. The light beam 12 propagates through a fluid channel 13 and strikes the inner surface of the inner capillary 14 at an angle $\theta_{C1}$. When passing the fluid-glass-boundary, the incident beam 12 is refracted towards the normal 15. The angle $\theta_{C2}$ of the refracted beam 16 relative to the normal 15 may be determined from Snell's law:

$$n_{fluid} \cdot \sin(\theta_{C1}) = n_{glass} \cdot \sin(\theta_{C2}).$$

with $n_{fluid}$ denoting the refractive index of the fluid flowing in the fluid channel 13, and with $n_{glass}$ denoting the refractive index of glass.

Next, the refracted beam 16 strikes the glass-liquid-boundary at the outer surface of the inner capillary 14. The liquid in the interspace 17 is selected to be less dense than glass, and therefore, total internal reflection will occur as soon as the angle of incidence of the refracted beam 15 exceeds the critical angle $\theta_{C2}$. The critical angle $\theta_{C2}$ can be determined by assuming that the refracted ray travels along the boundary. Hence, with regard to the critical angle $\theta_{C2}$, Snell's law can be written as:

$$n_{fluid} \cdot \sin(\theta_{C1}) = n_{glass} \cdot \sin(\theta_{C2}) = n_{inter} \cdot \sin(90°) = n_{inter},$$

with $n_{fluid}$ denoting the refractive index of the fluid flowing in the fluid channel 13, with $n_{glass}$ denoting the refractive index of glass, and with $n_{inter}$ denoting the refractive index of the medium in the interspace 17. From this equation, the critical angle $\theta_{C1}$ for a light beam propagating through the fluid channel 13 can be obtained as:

$$\theta_{C1} = \arcsin(n_{inter}/n_{fluid}).$$

With $n_{inter}=1$ and $n_{fluid}$ 1.33, a critical angle $\theta_{C1}$ of about 48.6° is obtained. Therefore, a light beam 12 that is incident on the inner capillary's inner surface at a flat angle of more than 48.6° relative to the normal 15 is reflected at the inner capillary's outer surface, with the reflected beam 18 being redirected towards the fluid channel 13.

In FIG. 1, the light beam 7 strikes the inner surface of the inner capillary 1 at an angle $\theta 1$. If $\theta_1$ is greater than the critical angle, the light beam 7 will we repeatedly reflected by the walls of the inner capillary 1. Therefore, most of the light that is coupled to the inner capillary 1 will remain within the inner capillary 1 and propagate along the direction of the fluid channel 4.

The outer capillary 2 is at least in sections adapted for sealing and protecting the inner capillary 1. In particular, it prevents dirt and/or moisture to adhere to the outer surface of the inner capillary 1 and impair the reflective properties of the inner capillary's outer surface.

Due to the presence of the interspace liquid, it is made sure that the light beam 7 is reliably reflected at the outer surface of the inner capillary 1. For further protection, the outer capillary 2 may be enclosed by a cladding. However, the presence of a cladding will not effect the reflective properties of the inner capillary 1, because total reflection occurs at the boundary between the inner capillary 1 and the interspace 3.

A fluid conduit of the type shown in FIG. 1 may be used for analyzing optical properties of a fluid passing through the inner capillary 1. For example, the fluid conduit may be part of a fluid cell. For example, typical dimensions for realizing a fluid cell may be as follows: the fluid conduit may comprise an inner capillary having an inner diameter of 300 µm and an outer diameter of 400 µm. The inner capillary may be enclosed by an outer capillary with an inner diameter of 500 µm, the outer capillary having an outer diameter of 700 µm. In this embodiment, an interspace of about 50 µm is formed between the outer surface of the inner capillary and the inner surface of the outer capillary.

Figure 3:
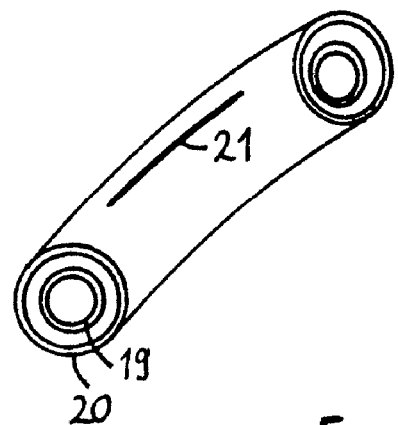
FIG. 3 shows the inner capillary touching the outer capillary at a line of contact.

A fluid conduit of the kind shown in FIG. 1 may be bent, at least to a certain extent. When the fluid conduit is slightly bent, as shown in FIG. 3, the inner capillary 19 gets in touch with the outer capillary 20 along a line of contact 21. Hence, for the overwhelming part of the inner capillary's outer surface, there still is some interspace between the inner and the outer capillary, which is an important issue in view of the inner capillary's reflective properties.

Figure 4A:
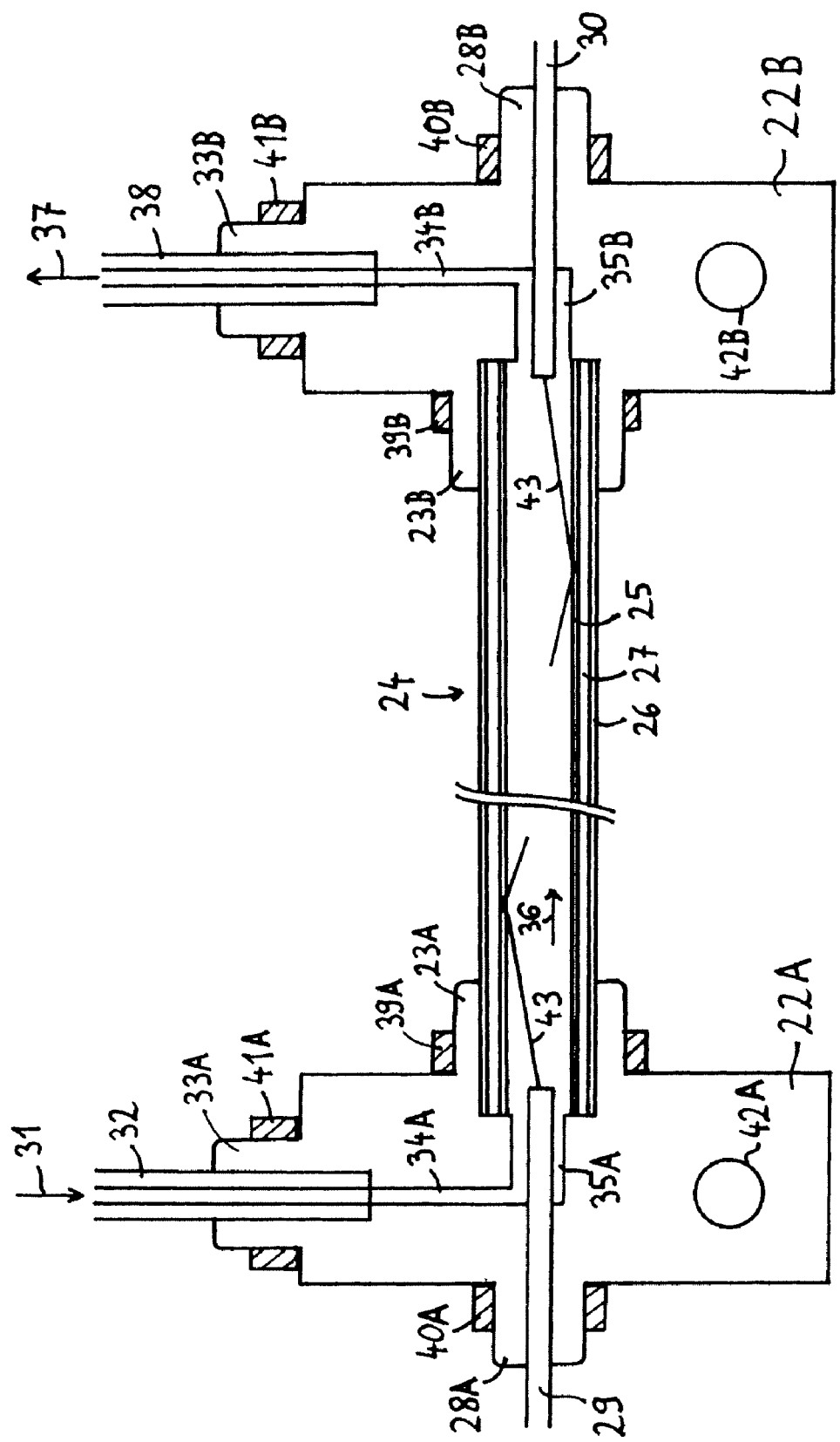
FIGS. 4A and 4B show fluid cells according to embodiments of the present invention.

A fluid conduit of the type shown in FIGS. 1, 2 and 3 may preferably be used as part of a detection cell, with the detection cell being adapted for monitoring one or more optical properties of a fluid passing through the fluid conduit. FIG. 4A shows a detection cell according to an embodiment of the present invention. The detection cell comprises a first connecting member 22A and a second connecting member 22B, with each of the connecting members 22A, 22B comprising a respective mount 23A, 23B for a fluid conduit 24. The fluid conduit 24 is a fluid conduit according to an embodiment of the present invention and comprises an inner capillary 25 and an outer capillary 26, with an interspace 27 being formed between the inner and the outer capillary. The interspace 27 is filled with an interspace liquid allowing total reflection at the boundary between the outer surface of the inner capillary 25 and the interspace 27. The first connecting member 22A further comprises a cylindrical mount 28A for fixing a first optical fiber 29. Via the first optical fiber 29, light may be coupled into the fluid conduit 24. Similarly, the second connecting member 22B comprises a cylindrical mount 28B for fixing a second optical fiber 30. The second optical fiber 30 is adapted for decoupling light from the fluid conduit 24.

In the embodiment shown in FIG. 4A, the first optical fiber 29 extends into the inner capillary 25. Thus, most of the light emitted by the first optical fiber 29 is coupled to the inner capillary 25. The second optical fiber 30 also extends into the inner capillary 25. However, the first and the second optical fiber 29, 30 do not have to extend into the inner capillary 25. For example, according to an alternative embodiment, the end face of the first optical fiber 29 may be positioned in front of the inlet of the fluid conduit, vis-à-vis the front face of the inner capillary 25. In this embodiment, the diameter of the first optical fiber 29 may even be larger than the inner diameter of the inner capillary 25. The end face of the first optical fiber 29 may either be in direct contact with the front face of the inner capillary 25, or there may be some distance between the end face of the first optical fiber 29 and the front face of the inner capillary 25. The second optical fiber 30 may be positioned behind the rear face of the fluid conduit, vis-à-vis the outlet of the inner capillary 25. The front face of the second optical fiber 30 may either be in direct contact with the rear face of the inner capillary 25, or there may be some distance between the front face of the second optical fiber 30 and the rear face of the inner capillary 25.

A flow 31 of fluid may be supplied to the fluid conduit 24 via an inlet pipe 32. The inlet pipe 32 may for example be a glass capillary. The inlet pipe 32 is fixed in a corresponding mount 33A of the first connecting member 22A. Via a channel 34A and a hollow section 35A, the flow of fluid is supplied to the fluid conduit 24. Thus, in the fluid conduit 24, a flow 36 of fluid is established. At the second connecting member 22B, a flow 37 of fluid is withdrawn via a hollow section 35B, a channel 34B and an outlet pipe 38. The outlet pipe 38, which may for example be a glass capillary, is fixed in a mount 33B.

For sealing the fluid connections of the first connecting member 22A, each of the mounts 23A, 28A and 33A is secured with a metal ring 39A, 40A, 41A that is slid on the respective mount. Then, the rings 39A, 40A, 41A are subjected to a high frequency magnetic field of about 600 MHz. During this treatment, the plastics material of the mounts 23A, 28A and 33A melts at least partially and acts as a hot-melt adhesive. As a result of the thermal bonding process, fluid-tight connections are established at each of the mounts 23A, 28A, 33A. These connections may withstand pressures of up to 50 bar.

Correspondingly, at the second connecting member 22B, the mounts 23B, 28B and 33B are provided with metal rings 39B, 40B, 41B. Then, the respective mounts 23B, 28B, 33B are also subjected to a heat bonding process, in order to establish fluid-tight connections.

Each of the first connecting member 22A and the second connecting member 22B may e.g. comprise a respective mounting hole 42A, 42B for fastening the respective connecting member 22A, 22B. However, the mounting holes 42A, 42B are optional and not required for proper operation of the detection cell.

For analyzing optical properties of a fluid passing through the fluid conduit 24, a light beam 43 is coupled into the fluid conduit 24 via the first optical fiber 29. While traversing the fluid conduit 24, the light beam 43 is reflected several times at the outer surface of the inner capillary 25 before being received by the second optical fiber 30. The light received by the second optical fiber 30 is analyzed, and from the result of this analysis, the optical properties of the fluid passing through the fluid conduit 24 may be derived. For example, the presence of light-absorbing moieties in the fluid may lead to a corresponding intensity attenuation at certain wavelengths of the received light. The extent of intensity attenuation can be related to the concentration of the light-absorbing moiety in solution.

Figure 4B:
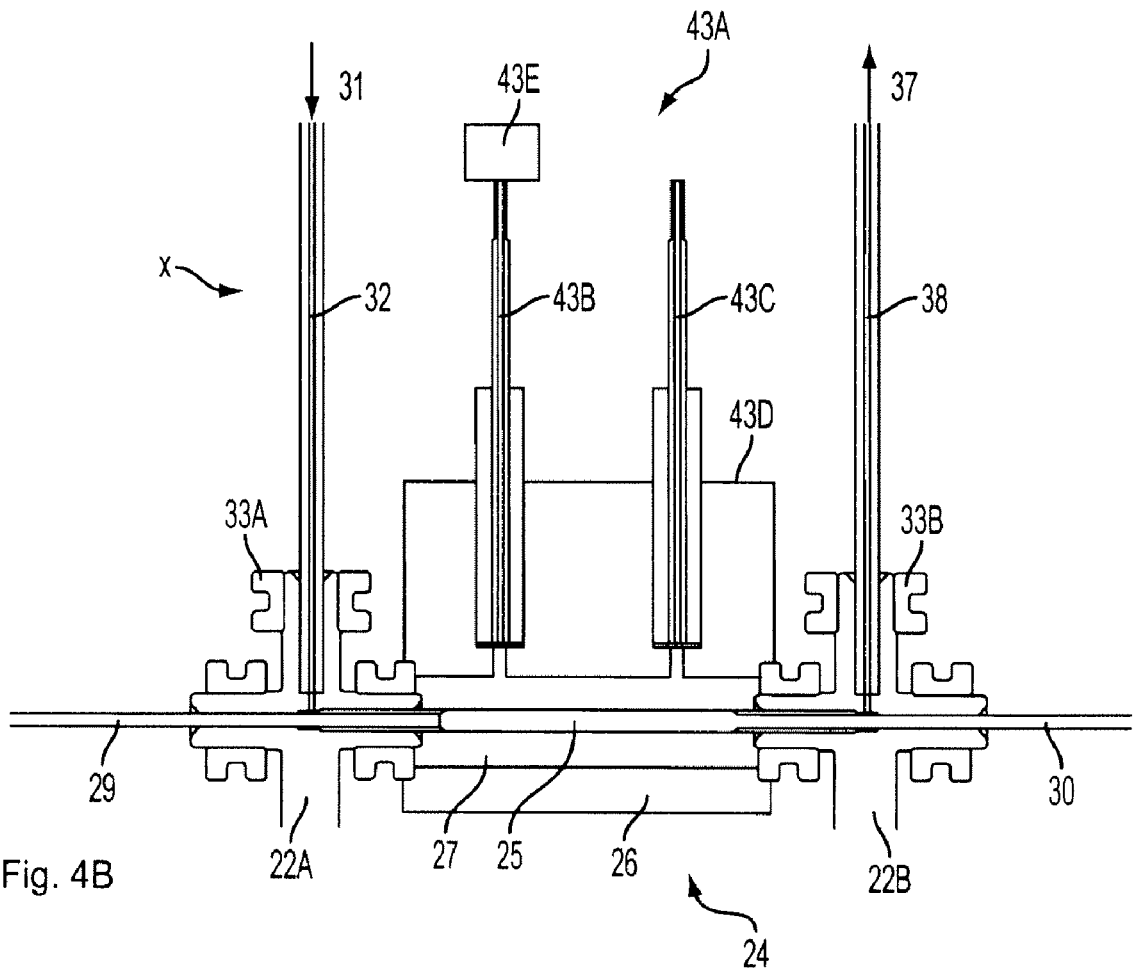

FIG. 4B illustrates an alternative fluid cell embodiment, which substantially corresponds to the embodiment of FIG. 4A, so that only the differing features shall be further described. Coupled to the fluid conduit 24 is a liquid conveyance unit 43A, which is configured to supply the interspace liquid into the interspace 27, and might further allow to pressurize the interspace liquid, i.e. to set the interspace liquid under pressure and/or maintain such pressure at least during operation of the fluid cell. In an alternative embodiment, the liquid conveyance unit 43A might alternatively or in addition allow varying a property of the interspace liquid (such as consistency, temperature, mixing ratio, electrical and/or thermal capacity, refractive index, etc.) and/or varying the pressure of the interspace liquid in the interspace 27.

The liquid conveyance unit 43A comprises an input conduit 43B and might also comprise an outlet conduit 43C. Both input and output conduits 43B and 43C can comprise or be, for example, a capillary e.g. made of glass or metal. Further, both input and output conduits 43B and 43C fluidically couple to the interspace 27, thus allowing to provide and/or remove interspace liquid into the interspace 27. The input and output conduits 43B and 43C can be fitted to or into a housing 43D, which may be part of the fluid conduit 24 and may abut to outer capillary 26 and thus to the interspace 27. While it is also possible to provide only one of the conduits 43B and 43C to fluidically couple to the interspace 27 to provide and/or remove interspace liquid into the interspace 27, providing two conduits 43B and 43C allows to better control flow of the interspace liquid, e.g. by reducing or avoiding air inclusions into the interspace. Further, providing two conduits also fosters varying the property of the interspace liquid (such as temperature).

At least one of the conduits 43B and 43C is coupled to a fluid supply (indicated in FIG. 4B by reference numeral 43E), which might comprise at least one of a pump, a container, and a valve, to supply the interspace liquid in to the interspace 27. The fluid supply 43E of the liquid conveyance unit 43A might further allow to pressurize the interspace liquid. This can be done, for example, by pumping the interspace liquid under pressure through the input conduit 43B, and then closing the output conduit 43C. The input conduit 43B might then be closed as well to maintain the pressure. Alternatively, the fluid supply 43E may continuously pressurize. Closing the conduits 43B and/or 43C can be done by any means known in the art, such as clamping, screw fitting, use of check valves, or for example just by squeezing the capillaries. The fluid supply 43E may also allow varying the pressure of the interspace liquid in the interspace 27, e.g. by means of a pump or a syringe.

The fluid supply 43E may further ally varying a property of the interspace liquid (such as consistency, mixing ratio, temperature, electrical and/or thermal capacity, refractive index, etc.) in the interspace 27. This can be done, for example, by providing adequate mixing functionality (e.g. plural different liquids, valves, etc.) as readily known in the art, use of a pump, and/or a heat exchanger, etc.

Figure 5:
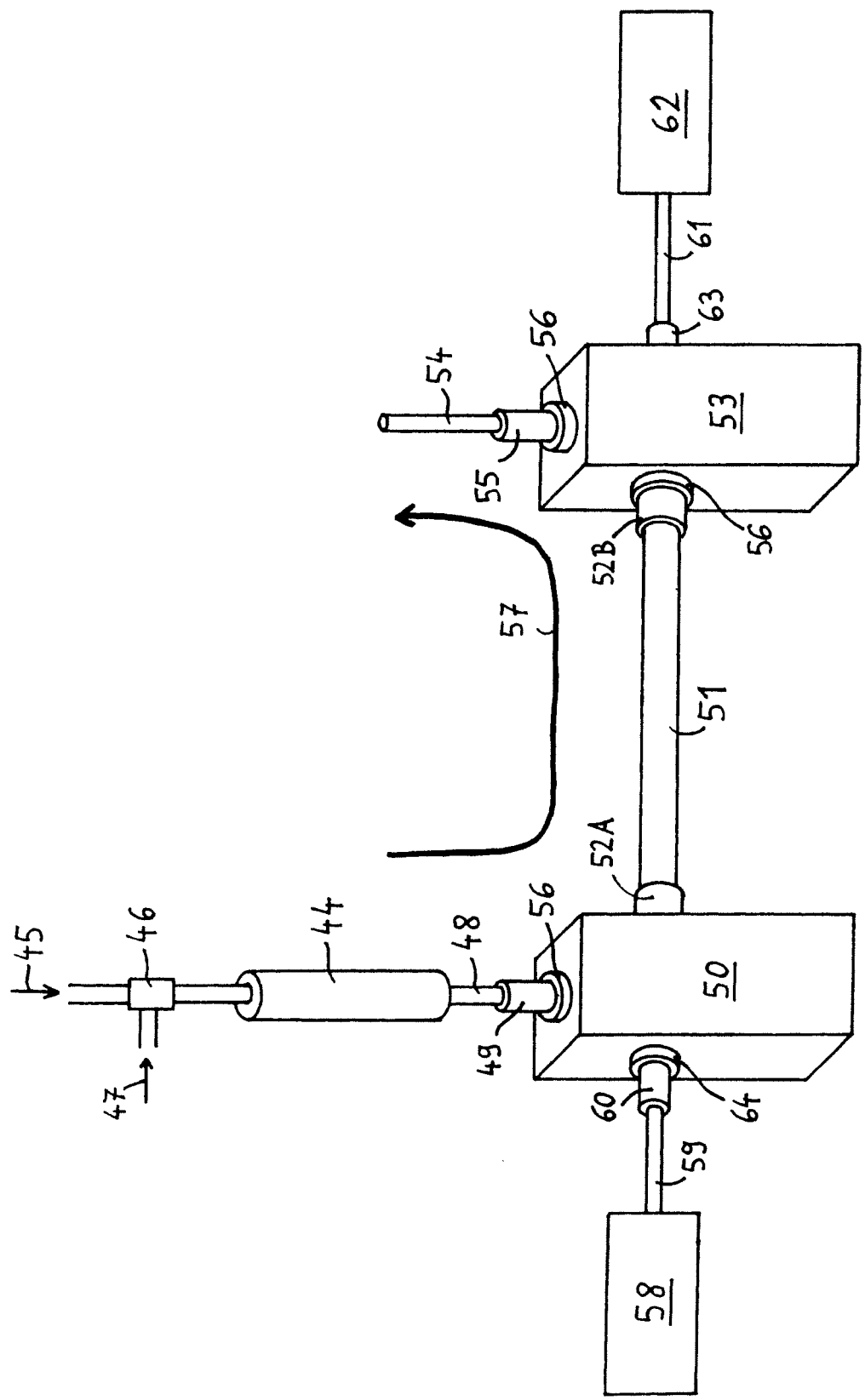
FIG. 5 depicts a separation system comprising a fluid cell according to an embodiment of the present invention.

According to a preferred embodiment, the fluid cells shown in FIGS. 4A and 4B may be employed for detecting sample compounds that have been separated by a sample separation device. FIG. 5 illustrates a sample separation system comprising a separation device 44 that is fluidically coupled with a detection cell of the type shown in FIG. 4. The separation device 44 may for example be a liquid chromatography column, an electrophoresis column, an electrochromatography column, or any other separation device adapted for separating compounds of a fluid sample. The separation device 44 may be filled with a stationary phase, like for example silica gel. A flow of mobile phase 45 is supplied to the separation device 44 and passes through a sample injection unit 46. At the sample injection unit 46, a volume 47 of fluid sample may be supplied to the mobile phase. The fluid sample is conveyed through the separation device 44. During their passage through the separation device 44, the sample's compounds are separated. The mobile phase and the sample's compounds are supplied, via a pipe 48 and a mount 49, to a first connecting member 50. There, the flow is redirected towards the fluid conduit 51. The fluid conduit 51 is a fluid conduit according to embodiments of the present invention and comprises an inner capillary surrounded by an outer capillary. The fluid conduit 51 is fixed between a first mount 52A and a second mount 52B and provides a fluidic connection between the first connecting member 50 and a second connecting member 53. At the second connecting member 53, the flow of fluid passing through the fluid conduit 51 is directed towards an outlet pipe 54, which is attached to the second connecting member 53 via a mount 55. To establish fluid-tight connections, the mounts 49, 52A, 52B, 55 are secured with metal rings 56. Arrow 57 indicates the path of the mobile phase and the separated sample compounds. The mobile phase with the separated compounds is passed from the outlet of the separation device 44 via the pipe 48 and the fluid conduit 51 to the outlet pipe 54.

For analyzing at least one optical property of the fluid passing through the fluid conduit 51, light from a light source 58 is coupled into the fluid conduit 51. The light source 58 may for example be a laser that provides light of one well-defined wavelength, or a set of different wavelengths. Alternatively, the light source 58 may supply a continuous spectrum of different wavelengths to the fluid conduit 51. For example, a mercury vapor lamp may be used as a light source. The light from the light source 58 is forwarded to the first connecting member 50 via a first optical fiber 59 that is fixed in a fiber connector 60. The light from the light source 58 is coupled into the fluid conduit 51, traverses the fluid conduit 51 and interacts with sample compounds that pass through the fluid conduit 51. At the second connecting member 53, the light is decoupled from the fluid conduit 51. Via a second optical fiber 61, the light is forwarded to a detection unit 62. The second optical fiber 61 is fixed in a fiber connector 63, the fibre connections being secured with metal rings 64.

At the detection unit 62, the optical properties of the received light are analyzed. The detection unit 62 may e.g. be adapted for monitoring the intensity of the received light at one or more different wavelengths. The detection unit 62 may as well analyze other optical properties of the received light, like e.g. properties related to polarization. The detection unit 62 may e.g. be a variable wavelength detector (VWD) that detects the received light's intensity at several discrete wavelengths. Alternatively, the detection unit 62 may e.g. be a diode array detector (DAD). A diode array detector is adapted for splitting up the received light into its spectral components, wherein an array of photosensitive elements is employed for determining the respective intensities of the spectral components. Hence, a diode array detector is operative to monitor a spectral range of intensity values of a light signal.

Figure 6:
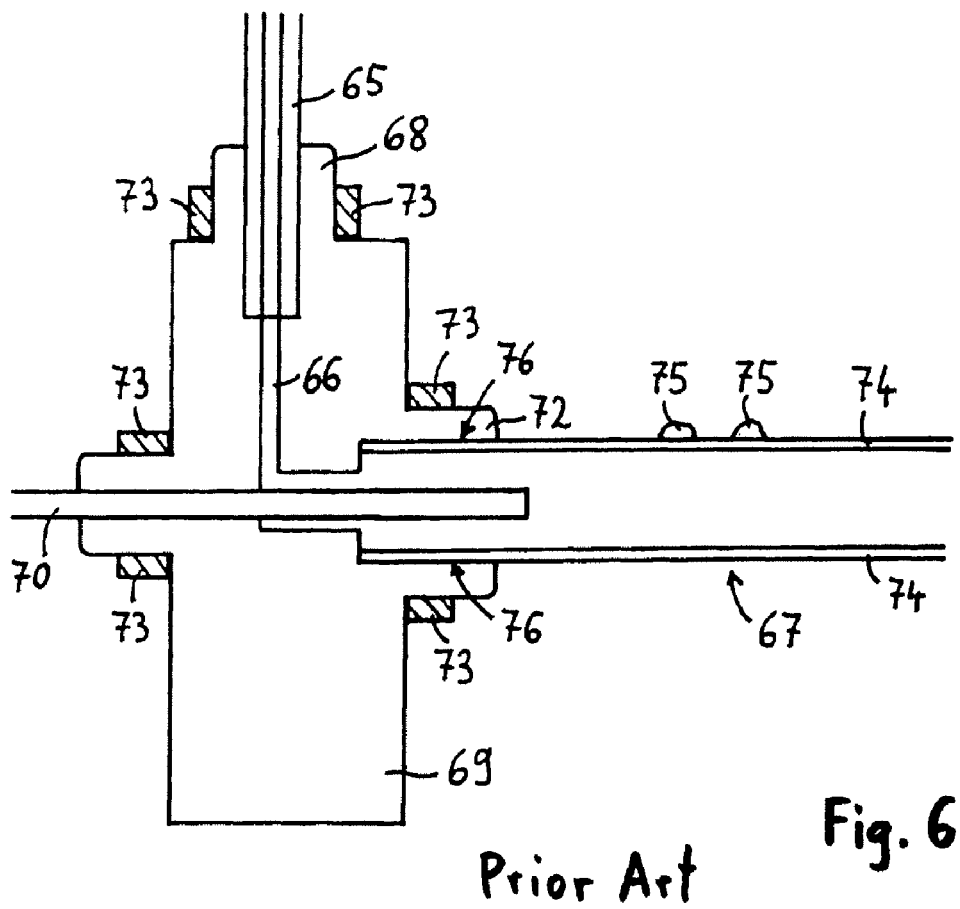
FIG. 6 shows a fluid conduit according to the prior art.

To further illustrate the differences of embodiments of the present invention vis-à-vis the prior art, FIG. 6 depicts a fluid cell according to a prior art solution. Via an inlet pipe 65 and a channel 66, fluid is supplied to a fluid conduit 67, with the inlet pipe 65 being fixed in a mount 68 of a connecting member 69. Light is coupled into the fluid conduit 67 via an optical fiber 70 that is fixed in a mount 71. The connecting member 69 further comprises a mount 72 for fixing the fluid conduit 67. Each of the mounts 68, 71, 72 is secured by a respective metal ring 73.

In contrast to the embodiments of the present invention, the fluid conduit 67 according to the prior art solely comprises one single capillary 74. A beam of light coupled into the fluid conduit 67 is reflected at the outer surface of the capillary 74. Therefore, as shown in FIG. 6, the presence of dirt and dust 75 may impair the reflective properties of the capillary's outer surface. Furthermore, in the region 76, the outer surface of the capillary 74 adjoins to the plastics material of the mount 72, and therefore, there is no glass-air boundary, which may impair total reflection. Due to the unsatisfactory reflection properties in the region 76, the optical fiber 70 has to extend quite far into the fluid conduit 67, which may give rise to undesired vibrations of the optical fiber 70.

By employing a fluid conduit comprising an inner capillary and an outer capillary as shown in FIGS. 1, 2, and 3, the disadvantages of the fluid conduit 64 of the prior art can be overcome. In particular, by employing a fluid conduit comprising an inner capillary and an outer capillary, reliable reflective properties are ensured across the entire length of the fluid conduit. In particular, the presence of a mount, such as e.g. the mount 72 shown in FIG. 6, does not impair the reflective properties of the fluid conduit.

This allows for implementations that have not been possible hitherto. For example, by using a fluid conduit according to embodiments of the present invention, light emitted by a light source may be coupled directly into the fluid conduit by focusing the light onto the fluid conduit's inlet.

Figure 7:
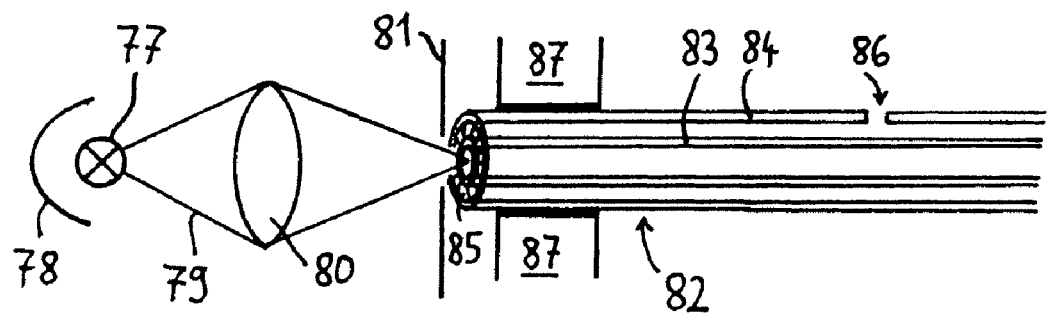
FIG. 7 illustrates how light emitted by a light source may be coupled into a fluid conduit without using an optical fiber.

FIG. 7 shows an embodiment of this type. A mercury vapor lamp 77 with a reflector 78 generates light 79 with a spectrum of different wavelengths. By means of a lens 80 and a diaphragm 81, the light emitted by the mercury vapor lamp 77 is focused onto the inlet of a fluid conduit 82, which is a fluid conduit according to an embodiment of the present invention. The fluid conduit 82 comprises an inner capillary 83 and an outer capillary 84 that encloses the inner capillary 83. At the front face, the inner capillary 83 and the outer capillary 84 may be welded together, whereby a welding seam 85 is formed. The diaphragm 81 is adapted for preventing that light emitted by the mercury vapor lamp 77 is coupled into the interspace and into the outer capillary 84. Furthermore, the diaphragm 81 may prevent that light is coupled into the glass walls of the inner capillary 83. The diaphragm 81 may either be realized as a separate plate, or by depositing a non-transparent coating onto at least one of the inner capillary 83, the welding seam 85 and the outer capillary 84.

A diaphragm may also be useful in an embodiment where an optical fiber is used instead of a mercury vapor lamp 77, with the end face of the optical fiber being placed right in front of the welding seam 85. In this case, the diaphragm may prevent that light from the optical fiber is coupled into the interspace between the inner capillary 83 and the outer capillary 84.

According to a further preferred embodiment, the outer capillary 84 may comprise a bore hole 86 that provides an access to the interspace between the inner capillary 83 and the outer capillary 84. For this purpose, a bore hole 86 having a diameter of e.g. 50 μm may be sufficient. For example, via the bore hole 86, polluted gases that are formed during the welding process may be removed from the interspace. Hence, the bore hole 86 may be used for exchanging a gas volume contained in the interspace between the inner capillary 83 and the outer capillary 84. Alternatively, via the bore hole 86, the interspace between the inner capillary 83 and the outer capillary 84 may be evacuated.

Afterwards, the bore hole 86 may be sealed. The bore hole 86 may e.g. be sealed by depositing an adhesive onto the bore hole 86, or by subjecting the bore hole 86 to a hot flame that partly melts the outer capillary 84.

A fluid conduit of the type shown in FIG. 7 ensures well-defined reflective properties across its entire length. In particular, even at regions where the fluid conduit is in direct contact with a mount 87, it is made sure that incident light with an angle of incidence above the critical angle is totally reflected at the walls of the inner capillary 83.

Figure 8:
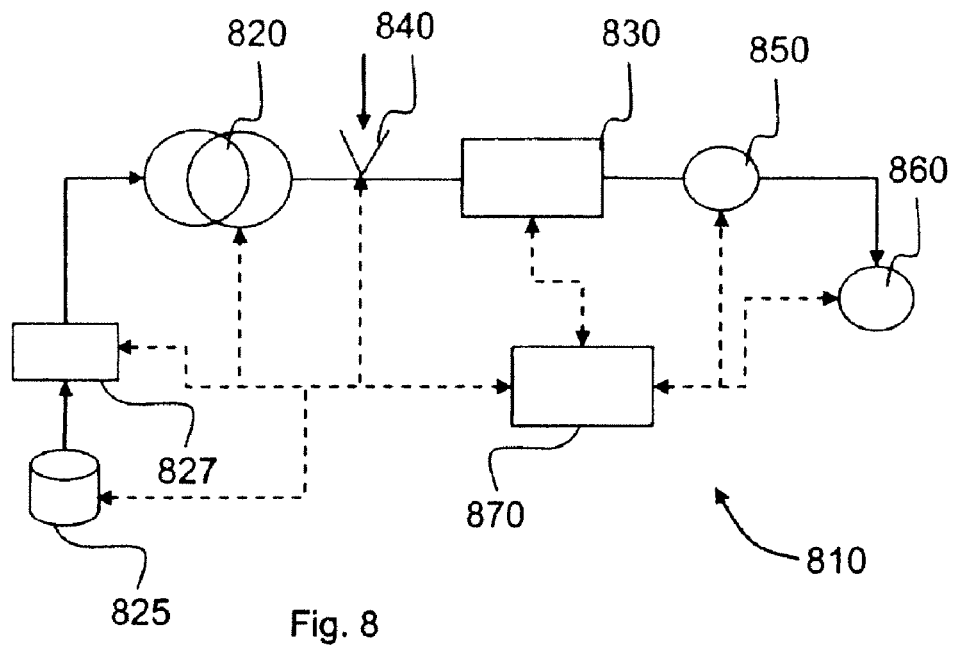
FIG. 8 shows a liquid separation system 810, in accordance with embodiments of the present invention, e.g. used in high performance liquid chromatography (HPLC).

FIG. 8 depicts a general schematic of a liquid separation system 810. A pump 820 receives a mobile phase from a solvent supply 825, typically via a degasser 827, which degases and thus reduces the amount of dissolved gases in the mobile phase. The pump 820—as a mobile phase drive—drives the mobile phase through a separating device 830 (such as a chromatographic column) comprising a stationary phase. A sampling unit 840 can be provided between the pump 820 and the separating device 830 in order to subject or add (often referred to as sample introduction) a sample fluid into the mobile phase. The stationary phase of the separating device 830 is adapted for separating compounds of the sample liquid. A detector 850 is provided for detecting separated compounds of the sample fluid. The detector 850 is preferably comprises a detection cell as illustrated in FIG. 4. A fractionating unit 860 can be provided for outputting separated compounds of sample fluid.

A data processing unit 870, which can be a conventional PC or workstation, might be coupled (as indicated by the dotted arrows) to one or more of the devices in the liquid separation system 810 in order to receive information and/or control operation. For example, the data processing unit 870 might control operation of the pump 820 (e.g. setting control parameters) and receive therefrom information regarding the actual working conditions (such as output pressure, flow rate, etc. at an outlet of the pump). The data processing unit 870 might also control operation of the solvent supply 825 (e.g. setting the solvent/s or solvent mixture to be supplied) and/or the degasser 827 (e.g. setting control parameters such as vacuum level) and might receive therefrom information regarding the actual working conditions (such as solvent composition supplied over time, flow rate, vacuum level, etc.). The data processing unit 870 might further control operation of the sampling unit 840 (e.g. controlling sample injection or synchronization sample injection with operating conditions of the pump 820). The separating device 30 might also be controlled by the data processing unit 870 (e.g. selecting a specific flow path or column, setting operation temperature, etc.), and send—in return—information (e.g. operating conditions) to the data processing unit 870. Accordingly, the detector 850 might be controlled by the data processing unit 870 (e.g. with respect to spectral or wavelength settings, setting time constants, start/stop data acquisition), and send information (e.g. about the detected sample compounds) to the data processing unit 870. The data processing unit 870 might also control operation of the fractionating unit 860 (e.g. in conjunction with data received from the detector 850) and provides data back.

The invention claimed is:

1. A fluid conduit comprising
an inner conduit configured for conducting a fluid, and
an outer conduit circumferentially enclosing the inner conduit,
wherein
the outer conduit's inner diameter is larger than the inner conduit's outer diameter, with an interspace being formed between the inner conduit's outer surface and the outer conduit's inner surface,
the interspace between the inner conduit's outer surface and the outer conduit's inner surface contains an interspace liquid with at least one varying property for modifying a behavior of the fluid conduit,
the inner conduit is configured for guiding light coupled into the inner conduit, and
dependent on the light's angle of incidence, total reflection occurs at a boundary between the inner conduit's outer surface and the interspace between the inner conduit and the outer conduit.

2. The fluid conduit of claim 1, wherein
the interspace liquid in the interspace has a refractive index lower than water.

3. The fluid conduit of claim 1, wherein
at one end or at both ends of the fluid conduit, the inner conduit and the outer conduit are welded together.

4. The fluid conduit of claim 1, wherein the length of the outer conduit differs from the inner conduit, and the interspace is sealed by adhering the conduits together or by sealing the outer conduit to a connecting member.

5. The fluid conduit of claim 1, further comprising
a liquid conveyance configured to supply the interspace liquid into the interspace.

6. The fluid conduit of claim 5, wherein
the liquid conveyance is configured to pressurize the interspace liquid.

7. The fluid conduit of claim 5, wherein
the liquid conveyance is configured to vary the at least one varying property of the interspace liquid.

8. The fluid conduit of claim 7, wherein
the property is at least one of: consistency, temperature, mixing ratio, electrical capacity, thermal capacity, refractive index, pressure.

9. The fluid conduit of claim 1, further comprising:
a first optical waveguide,
wherein a first end of the fluid conduit is configured for accepting the first optical waveguide, and the first optical waveguide being configured for coupling light into the fluid conduit.

10. The fluid conduit of claim 1, further comprising:
a second optical waveguide,
wherein a second end of the fluid conduit is configured for accepting the second optical waveguide, the second optical waveguide being configured for decoupling light from the fluid conduit.

11. The fluid conduit of claim 1, further comprising:
at a first end of the fluid conduit, a flow of fluid is supplied to the inner conduit, and
at a second end of the fluid conduit, a flow of fluid is withdrawn from the inner conduit.

12. A detection system comprising
a fluid conduit according to claim 1,
a first connecting member attached to the fluid conduit's first end, the first connecting member comprising a fluid inlet fluidically coupled to the fluid conduit, the fluid inlet being configured for supplying a flow of fluid to the fluid conduit, the first connecting member being further configured for coupling light into the fluid conduit, and
a second connecting member attached to the fluid conduit's second end, the second connecting member comprising a fluid outlet fluidically coupled to the fluid conduit, the fluid outlet being configured for withdrawing a flow of fluid that has been conveyed through the fluid conduit, the second connecting member being further configured for decoupling light from the detection channel.

13. The detection system of claim 12, further comprising:
a first optical waveguide configured for coupling light into the fluid conduit,
the first connecting member is configured for accepting the first optical waveguide,
the first optical waveguide extends into the fluid conduit,
the first optical fiber is positioned in front of the fluid conduit's first end, and
the first optical fiber is positioned face to face with the fluid conduit's first end.

14. The detection system of claim 12, further comprising:
a second optical waveguide configured for decoupling light from the fluid conduit,
the second connecting member is configured for accepting the second optical waveguide, and
the second optical waveguide extends into the fluid conduit.

15. The detection system of claim 14, wherein
the first and the second connecting members are made of plastic material, preferably of PEEK.

16. The detection system of claim 12, further comprising
a light source configured for supplying light to the fluid conduit.

17. The detection system of claim 12, wherein the detection system is configured for at least one of:
determining at least one optical property of a fluid passing through the fluid conduit as a function of time;
monitoring absorbance of a fluid passing through the fluid conduit as a function of time.

18. A fluid separation system for separating compounds of a sample fluid in a mobile phase, the fluid separation system comprising:
- a mobile phase drive configured to drive the mobile phase through the fluid separation system,
- a separation unit configured for separating compounds of the sample fluid in the mobile phase, and
- a detection system of claim 8 configured to detect separated compounds of the sample fluid.

19. The fluid separation system of claim 18, further comprising at least one of:
- a sample injector configured to introduce the sample fluid into the mobile phase;
- a collection unit configured to collect separated compounds of the sample fluid;
- a data processing unit configured to process data received from the fluid separation system;
- a degassing apparatus for degassing the mobile phase.

* * * * *